United States Patent
Carmi

(10) Patent No.: US 10,803,633 B2
(45) Date of Patent: Oct. 13, 2020

(54) SYSTEMS AND METHODS FOR FOLLOW-UP FUNCTIONAL IMAGING

(71) Applicant: General Electric Company, Schenectady, NY (US)

(72) Inventor: Raz Carmi, Haifa (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 362 days.

(21) Appl. No.: 15/889,757

(22) Filed: Feb. 6, 2018

(65) Prior Publication Data
US 2019/0244398 A1    Aug. 8, 2019

(51) Int. Cl.
G06T 11/00 (2006.01)
G16H 30/20 (2018.01)
G16H 10/60 (2018.01)
G06T 7/00 (2017.01)

(52) U.S. Cl.
CPC .......... G06T 11/008 (2013.01); G06T 7/0012 (2013.01); G06T 7/0016 (2013.01); G16H 10/60 (2018.01); G16H 30/20 (2018.01); G06T 2207/10081 (2013.01); G06T 2207/10104 (2013.01); G06T 2207/10108 (2013.01); G06T 2211/40 (2013.01)

(58) Field of Classification Search
CPC ... G06T 11/008; G06T 7/0012; G06T 7/0016; G16H 10/60; G16H 30/20
See application file for complete search history.

(56) References Cited

U.S. PATENT DOCUMENTS

| | | |
|---|---|---|
| 6,728,424 B1 | 4/2004 | Zhu et al. |
| 6,740,883 B1 | 5/2004 | Stodilka et al. |
| 6,878,941 B2 | 4/2005 | Balan et al. |
| 7,348,564 B2 | 3/2008 | Wollenwebber et al. |

(Continued)

FOREIGN PATENT DOCUMENTS

WO    2009138898 A1    11/2009

OTHER PUBLICATIONS

Wang, Zhou, Eero P. Simoncelli, and Alan C. Bovik. "Multiscale structural similarity for image quality assessment." The Thrity-Seventh Asilomar Conference on Signals, Systems & Computers, 2003. vol. 2. Ieee, 2003. (Year: 2003).*

(Continued)

Primary Examiner — Vincent Rudolph
Assistant Examiner — Raphael Schwartz
(74) Attorney, Agent, or Firm — The Small Patent Law Group LLC; Dean D. Small

(57) ABSTRACT

A method is provided for follow-up functional imaging after obtaining a first functional image data set of a patient. The method includes obtaining a second functional image data set of the patient at a follow-up time subsequent to the obtaining of the first functional image data set. The method also includes generating a local change map using the first functional image data set and the second functional image data set. Further, the method includes generating a mutual structural similarity map using the first functional image data set and the second functional image data set. Also, the method includes generating a significant-response map using the local change map and the mutual structural similarity map. The method also includes displaying the significant-response map.

20 Claims, 5 Drawing Sheets

(56) References Cited

U.S. PATENT DOCUMENTS

| | | | |
|---|---|---|---|
| 2003/0004405 A1 | 1/2003 | Townsend et al. | |
| 2003/0216631 A1 | 11/2003 | Bloch et al. | |
| 2004/0071325 A1 | 4/2004 | Declerck et al. | |
| 2005/0226527 A1 | 10/2005 | Weese et al. | |
| 2007/0258908 A1 | 4/2007 | Lanza et al. | |
| 2008/0064949 A1 | 3/2008 | Hertel et al. | |
| 2008/0095414 A1 | 4/2008 | Desh et al. | |
| 2008/0123922 A1 | 5/2008 | Gielen et al. | |
| 2009/0202125 A1 | 8/2009 | Zhao et al. | |
| 2013/0129168 A1* | 5/2013 | Ross | G06T 7/0012 382/128 |
| 2016/0104301 A1* | 4/2016 | Liu | G06T 11/001 382/162 |
| 2016/0174895 A1 | 6/2016 | Ross et al. | |

OTHER PUBLICATIONS

Russakoff, Daniel B., et al. "Image similarity using mutual information of regions." European Conference on Computer Vision. Springer, Berlin, Heidelberg, 2004. (Year: 2004).*

Nasr, M. Abdel-Salam, Mohammed F. AlRahmawy, and A. S. Tolba. "Multi-scale structural similarity index for motion detection." Journal of King Saud University-Computer and Information Sciences 29.3 (2017): 399-409. (Year: 2017).*

Khullar, Siddharth, et al. "A new metric to measure shape differences in fMRI activity." Medical Imaging 2011: Image Processing. vol. 7962. International Society for Optics and Photonics, 2011. (Year: 2011).*

Russakoff et al, "Image Similarity Using Mutual Information of Regions", Regional Mutual Information, ECCV 2004: Computer Vision—ECCV 2004 pp. 596-607 (12 pages).

\* cited by examiner

SYSTEMS AND METHODS FOR FOLLOW-UP FUNCTIONAL IMAGING

BACKGROUND

The subject matter disclosed herein relates generally to medical imaging systems, and more particularly to follow-up analyses using functional imaging.

In functional medical imaging modalities, such as single photon emission computed tomography (SPECT) and positron emission tomography (PET), it is common to perform follow-up studies involving at least two scans of the same patient acquired at different times. Such procedures can indicate, for example, the physiological response to a certain medical treatment, and can help planning of further patient management. In the analysis of follow-up scans, the user/physician typically compares the image signals on relevant regions or organs and assesses the radiotracer activity differences. For example, if an identified lesion shows significantly reduced tracer uptake after a therapy course, this may indicate good response to the therapy procedure. Otherwise, if the lesion shows increased tracer uptake, this may indicate no response and progressive disease (i.e. medical condition deterioration). One group of techniques for such follow-up analysis utilizes fully automatic or semi-automatic segmentation of identified relevant regions in the image volume such as lesions or tumors. Another group of techniques is based on calculating voxel-based comparison maps. In such voxel-based maps, no segmentation may be required, which can save time. However, substantial challenges still exist for follow-up analysis using functional imaging.

One problem, for example, is that in many cases the administered radiotracer is highly non-specific to the relevant disease or medical condition. For example, even if the tracer is aimed to target a certain type of cancer, it may also accumulate in organs such as the liver, intestine, spleen, kidneys, or bladder, or, as additional examples, in highly glucose absorbing organs such as the brain and myocardium. Another problem is that the image signal in a relevant region may depend not only on the actual physiological staging or response of the relevant disease or medical condition, but also on other factors such as administered tracer dose, variable patient metabolism, liquids or food consumptions prior to the scan, residual tracer cleansing from the body, time passed between tracer injection to the scan, and/or imaging system settings and parameters, for example.

BRIEF DESCRIPTION

In accordance with an embodiment, a method is provided for follow-up functional imaging after obtaining a first functional image data set of a patient. The method includes obtaining a second functional image data set of the patient at a follow-up time subsequent to the obtaining of the first functional image data set. The method also includes generating a local change map using the first functional image data set and the second functional image data set. Further, the method includes generating a mutual structural similarity map using the first functional image data set and the second functional image data set. Also, the method includes generating a significant-response map using the local change map and the mutual structural similarity map. The method also includes displaying the significant-response map.

In accordance with another embodiment, an imaging system is provided that includes an imaging detector system, at least one processor, and a display unit. The imaging detector system is configured to acquire a first functional image data set of a patient, and to acquire a second functional image data set of the patient at a follow-up time subsequent to the obtaining of the first functional image data set. The at least one processor configured to generate a local change map using the first functional image data set and the second functional image data set; generate a mutual structural similarity map using the first functional image data set and the second functional image data set; and generate a significant-response map using the local change map and the mutual structural similarity map. The display unit is configured to display the significant-response map.

In accordance with another embodiment, a non-transitory computer readable storage medium is provided that has a computer program including instructions stored thereon. When executed by a computer, the instructions cause the computer to: obtain a first functional image data set of a patient from a first time; obtain a second functional image data set of the patient at a follow-up time subsequent to the obtaining of the first functional image data set; generate a local change map using the first functional image data set and the second functional image data set; generate a mutual structural similarity map using the first functional image data set and the second functional image data set; generate a significant-response map using the local change map and the mutual structural similarity map; and display the significant-response map.

DETAILED DESCRIPTION

Figure 1:
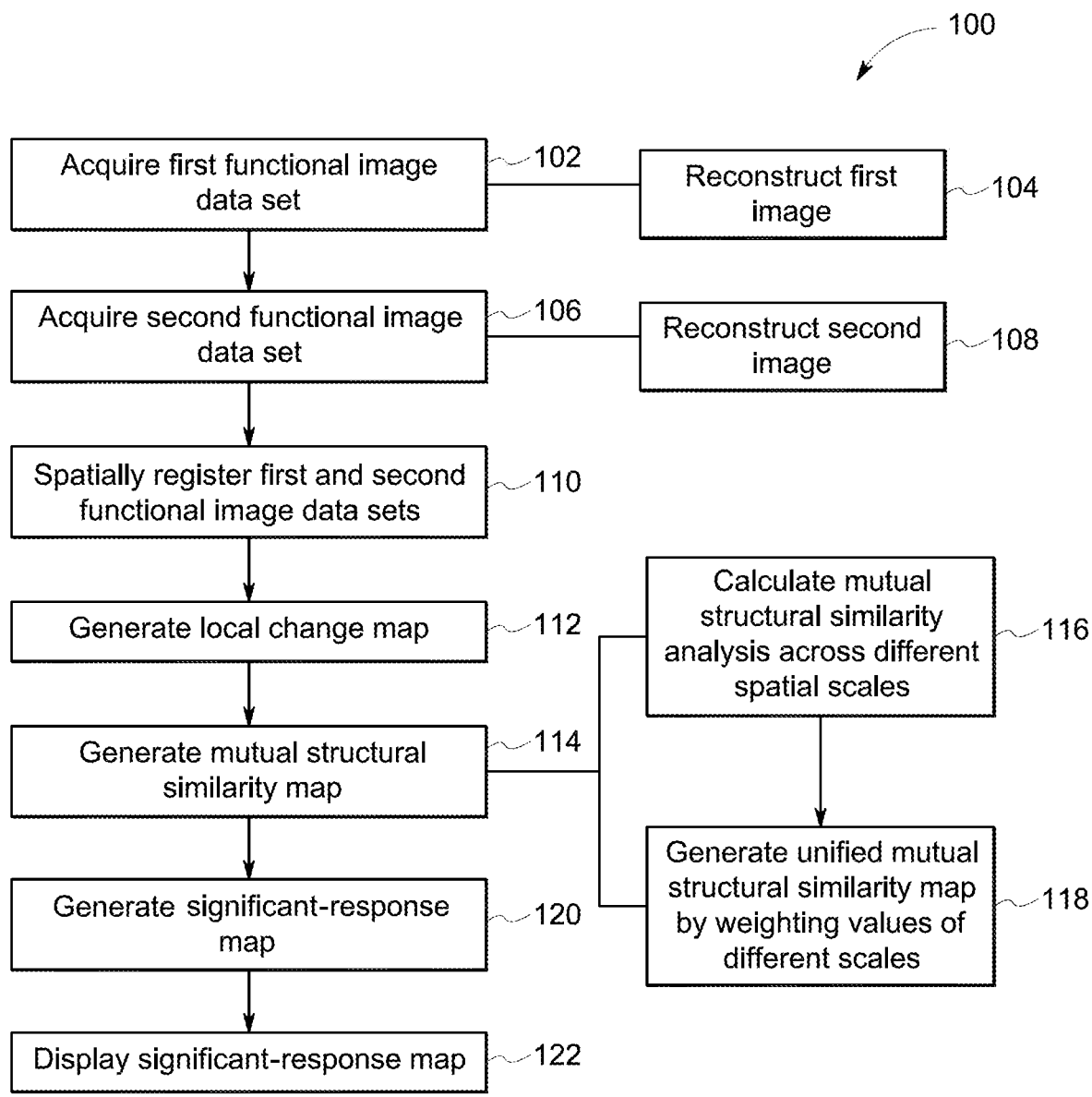
FIG. 1 shows a flowchart of a method, according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately modified by being programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for improved functional imaging in connection with follow-up analysis, for example. In various embodiments, a significant-response map is calculated and visualized. The significant-response map highlights or emphasizes the most relevant regions of an imaged volume in terms of functional response or change (e.g., between a reference image acquisition and a follow-up image acquisition). Various embodiments utilize both local signal change analysis (regarding, e.g., amount of activity level change) and local mutual structural similarity analysis (regarding, e.g., changes in structure without regard to activity level change, or with little or reduced regard to activity level change).

Various embodiments combine both image signal magnitude change (e.g., using a local change map) and a change in the corresponding local structures or shapes (e.g., using a mutual structural similarity map). For example, if a small lesion absorbs some tracer concentration in a first or reference scan, and the small lesion has completely disappeared on the follow-up scan, this may indicate excellent response even if the tracer concentration in the reference scan is not high by itself relative to some large internal organs. On the other hand, if a lesion shows high uptake signal in the reference scan and somewhat lower uptake in the follow-up scan, but exactly within the same structural distribution, this may indicate that the signal change is mostly due to the other irrelevant factors. Accordingly, various embodiments provide improved identification of relevant changes by considering both signal magnitude (e.g., uptake activity level) changes and structural changes in tandem with each other.

A technical effect of at least one embodiment includes improved imaging and image-based diagnosis. A technical effect of at least one embodiment includes improved identification of relevant changes in a follow-up functional imaging analysis. A technical effect of at least one embodiment includes improved diagnostic convenience and/or accuracy.

FIG. 1 provides a flowchart of a method 100 for imaging in accordance with various embodiments. The method 100 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be able to be used as one or more algorithms to direct hardware (e.g., one or more aspects of the processing unit 520) to perform one or more operations described herein.

At 102, a first functional image data set of a patient is acquired.

Generally, the first functional image data set, which may also be referred to herein as an initial image data set or a reference image data set, is acquired using a functional medical imaging modality. Functional imaging may also be referred to as physiological imaging, and includes imaging techniques directed to detecting or measuring changes in bodily function, such as metabolism, blood flow, regional chemical composition, or absorption. For example, a radiopharmaceutical or other agent may be administered to the patient, and the uptake of the radiopharmaceutical or agent may be detected to help measure or detect functional-related aspects of the patient. Examples of functional modalities that may be used in various embodiments include nuclear medicine (NM) imaging modalities, such as single photon emission computed tomography (SPECT) or positron emission tomography (PET) imaging. Other modalities such as ultrasound, computed tomography (CT), or magnetic resonance imaging (MRI) may also provide functional information and be used additionally or alternatively in various embodiments. It may be noted that, while functional imaging is directed to physiological activities, functional imaging data sets may also include structural information (e.g., various structures within the patient may uptake a given amount of the radiopharmaceutical or agent, or otherwise be visible within the image data set). At 104, a first image is reconstructed using the first functional image data set.

At 106, a second functional image data set of the patient is acquired. It may be noted that in various embodiments the first and/or second functional image data set may be acquired directly using a functional imaging system, or may be acquired from a database or other storage location that stores previously acquired imaging information. In various embodiments, the second functional image data set is acquired as a follow-up to the first, initial, or reference image data set, and is acquired at a follow-up time subsequent to the obtaining of the first functional image data set. For example, the first functional image data set may be acquired at an initial time before a course of treatment is initiated. Then, after the course of treatment has been implemented for a given amount of time, the second functional image data set may be acquired, for example, to help evaluate the progression of the patient and/or whether or not the course of treatment has been effective. In some embodiments, the follow-up time at which the second functional image data set is obtained or acquired may be at least two weeks after the initial time at which the first functional image data set is obtained. For example, the follow-up time may be a few weeks, or a few months, after the initial time. Further, multiple follow-up or additional functional image data sets may be acquired at different times over a course of treatment. The second functional image data set may be acquired using the same modality (or modalities) as the first function image data set. It may be noted that the first and second functional imaging data sets (and any additional function imaging data sets acquired) may be either 2D or 3D data sets. At 108, a second image is reconstructed using the second functional image data set.

At 110, the first functional imaging data set and the second functional imaging data set are spatially registered. For example, non-rigid registration techniques may be employed. The spatial registration may be partial or full. It may be noted that, with the functional imaging data sets acquired with considerable time in-between the corresponding acquisitions, the accuracy of the registration may not be very high. It may further be noted, however, that various methods employed herein do not require high registration accuracy, and most or all local misalignments that may arise may be dealt with or addressed using techniques discussed herein. Accordingly, it may be noted that, in some embodiments, the image data sets may not be spatially registered.

At 112, a local change map is generated using the first functional image data set and the second functional image data set. Generally, the local change map indicates differences (e.g., in uptake activity level) between the two image data sets. In some embodiments, local changes between image signals of the first and second functional image data sets are calculated or analyzed, and used to generate the local change map.

For example, local changes between the first and second functional image data sets (e.g., between a reference data set and a follow-up data set) are calculated in various embodiments for the purpose of determining or generating the local change map (which may be a voxel-based array) that represents the positive or negative effective change of the image signals between the first and second data sets (or between reference and follow-up data sets). In various embodiments, the local change analysis is performed on a small local voxel-neighborhood in such a way that relatively small mis-registration will not affect the results. For example, the analysis may check if a local activity distribution in the reference scan (or first functional image data set) increases or decreases in any of the points within a small corresponding region in the follow-up scan (or second functional image data set). Accordingly, if a small lesion from the first or reference data set identically appears in the second or follow-up data set, but with a small spatial shift, the difference between the first and second data sets corresponding to the small lesion will be interpreted or applied as no change. For additional examples and discussion regarding generating the local change map and related aspects, see FIG. 2 and the related discussion.

At 114, a mutual structural similarity map is generated. Generally, the mutual structural similarity map represents and/or corresponds to similarities in structures identified or detected in the first and second functional image data sets. The mutual structural similarity map is directed more to similarities (or differences) in size and/or shape of particular structures within an image volume, instead of being directed to relative changes in activity level. In various embodiments, the mutual structural similarity may be generated using the first functional image data set and the second functional image data set. For example, in the illustrated embodiment, at 116, a mutual structural similarity analysis is calculated across different spatial scales for the first and second functional image data sets. Then, at 118, a unified mutual structural similarity map is generated by weighting the mutual structural similarity analysis values of the different spatial scales.

In various embodiments, a mutual structural similarity analysis between the two data sets is employed in connection with generating the mutual structural similarity map. It may be noted that other types of analysis or techniques may be employed additionally or alternatively. Generally, the mutual structural similarity map is used to help determine whether a change of image signal between the first (or reference) functional image data set and the second (or follow-up) functional image data set also involves structural changes (e.g., changes in the structure of a patient, such as change in size of a lesion, addition of a lesion, removal of a lesion). In some embodiments, the analysis is performed over various different spatial scales. Use of different spatial scales in various embodiments helps to address potential structures at different sizes. In various embodiments, by weighting and combining analysis values generated, a unified mutual structural similarity map may be constructed or generated. For additional examples and discussion regarding generating the mutual structural similarity map and related aspects, see FIG. 3 and the related discussion.

At 120, a significant-response map is generated. In the illustrated embodiment, the significant-response map is generated using the local change map and the mutual structural similarity map. Accordingly, values on the significant-response map take into account both relative magnitude changes in uptake values as well as structural changes. For example, the significant-response map may display values (e.g., shades of colors corresponding to value ranges) for different voxels or locations of the patient volume, with values on the significant-response map increasing where the local change value (from the local change map) increases and where the structural similarity values (from the mutual structural similarity map) decreases.

Generally, the analyses (e.g., maps) from steps 112 and 114 are used to generate the significant-response map. In various embodiments, the significant-response map provides a visualization of those regions which significantly involve both activity changes and structural changes, or displays values indicating the relative significance of changes between the first (or reference) and second (or follow-up) functional image data sets. In various embodiments, a dedicated visualization application may be used to display the significant-response map and/or related aspects of related analyses to a user. In some embodiments, only those regions significantly involving both structural and activity level changes are shown or displayed as part of the significant-response map. For example, portions having both activity level and structural changes may be shown in colors or shades representing activity levels, while other portions are left clear or in a background color. The use of such a significant-response map in various embodiments helps speed the clinical assessment of follow-up images (and related courses of treatment), for example, by allowing a user to directly focus on the most relevant regions of an imaged volume. For additional examples and discussion regarding generating the significant-response map and related aspects, see FIG. 4 and the related discussion.

At 122, the significant-response map is displayed. In some embodiments, the significant-response map is displayed along with the reconstructed first image and/or the reconstructed second image. The significant-response map, for example, may be displayed alongside a corresponding reconstructed image and/or overlaid over a corresponding reconstructed image.

It may be noted that different embodiments may employ variations in one or more aspects from the examples discussed herein. For instance, additionally or alternatively to displaying the significant-response map or otherwise providing direct visualization results, approaches discussed herein may be used as a step or portion in a fully automated medical diagnostic application. In some embodiments, tumor-response classification algorithms may be applied directly on the significant-response maps rather than on raw image data of one or more follow-up scans. Such an approach may increase diagnostic accuracy. It may further be noted that such classification techniques may include machine-learning and/or deep-learning methods. As another example, a visualization scheme may be presented to a user in which regions that may be partially or fully masked (e.g., in step 120 discussed herein) due to relative insignificance may be shown using an appropriate color palette allowing areas of relatively insignificant change to be shown while still being distinguished from areas of more significant change. Also, it may be noted that in various medical application where manual segmentation by a user is still utilized or required, relevant structures may be segmented directly on the significant-response map instead of on raw image data. Another variation that may be employed in various embodiments is to utilize multiple follow-up scans (e.g., to generate additional functional image data sets such as a third functional image data set corresponding to a second follow-up, a fourth functional image data set corresponding to a third follow-up, and so on), and a unified analysis may be generated combining trends or changes between the multiple scans into a single map. Further still, it may be noted that algorithm parameters used in connection with one or more analyses discussed herein may be tuned or automatically learned, for example using a priori information.

Figure 2:
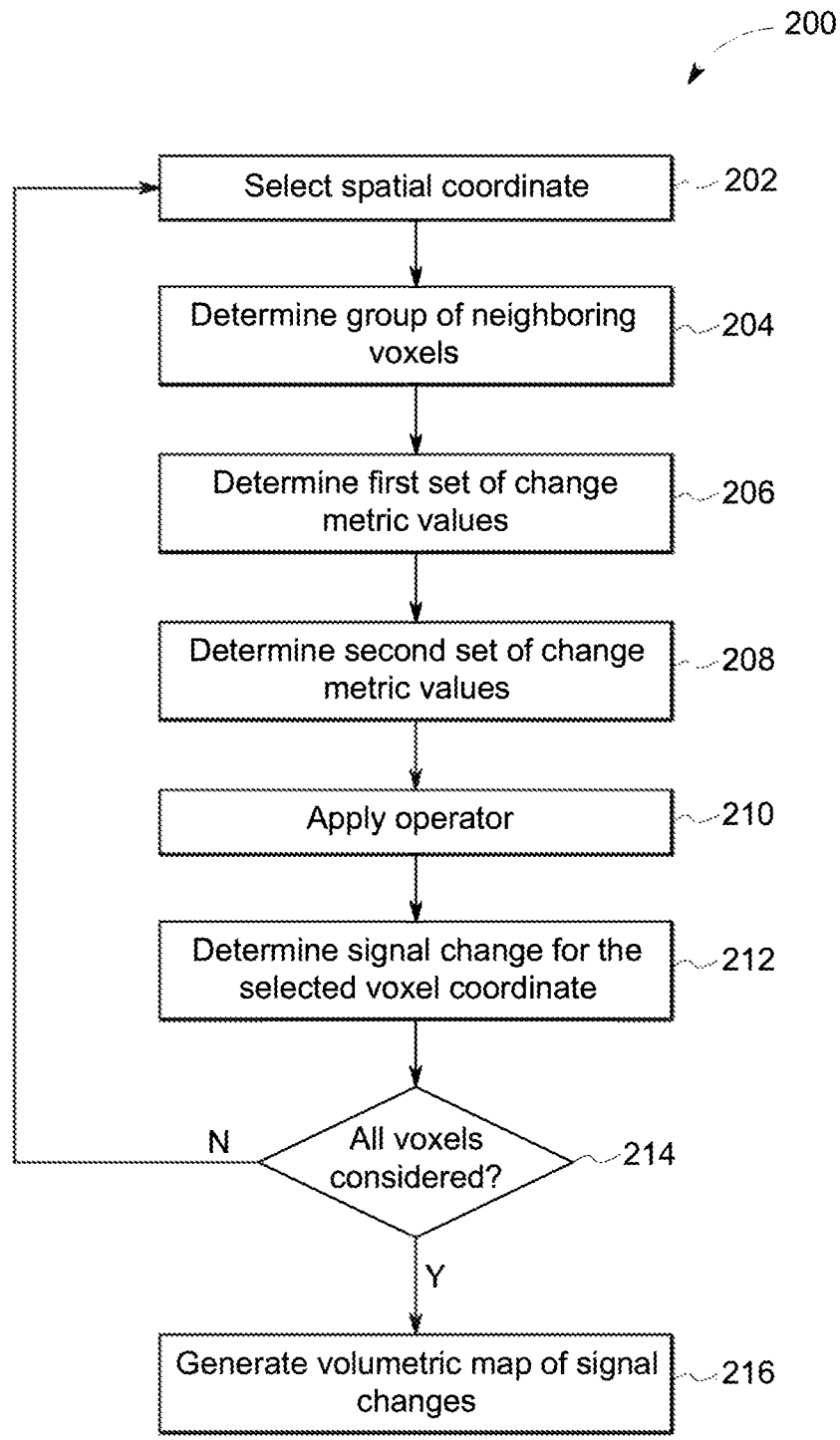
FIG. 2 shows a flowchart of a method, according to an embodiment.

FIG. 2 provides a flowchart of a method 200 for imaging in accordance with various embodiments (e.g., for generating a local change map for use in connection with method 100). The method 200 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be able to be used as one or more algorithms to direct hardware (e.g., one or more aspects of the processing unit 520) to perform one or more operations described herein.

At 202, a spatial coordinate is selected. In the illustrated embodiment, a voxel is selected. The voxel is selected from an imaged volume, with the imaged volume having been imaged at least twice (e.g., at a first or reference time and at a second or follow-up time), such that the voxel is included in at least two functional image data sets. It may be noted that, as the process continues, a number of voxels (e.g., all voxels shared between the two or more functional image data sets) will be selected in turn and processed. For example, an initial voxel with coordinates (x, y, z) and a value V1 from a first functional image data set may be the first voxel selected.

At 204, a group of neighboring voxels to the selected voxel are determined. For example, the group of neighboring voxels in various embodiments is from the image data set other than the image data set from which the voxel was selected. For example, with the voxel selected from the first functional image data set, neighboring voxels from the corresponding second functional image data set may be selected. In some embodiments, where the voxel selected has coordinates (x, y, z) in the first functional image data set, the neighboring voxels may be selected as a box within the second functional image data set defined by (x−d:x+d, y−d:y+d, z−d:z+d), where d is a predetermined parameter. For example, d may be set equal to 5 in various embodiments.

At 206, a first set of change metric values are determined. For example, the first set of change metric values in various embodiments are between a value of the voxel in the first functional image data set (e.g., the voxel selected at 202) and values of neighboring voxels in the second functional image data set (e.g., the box selected at 204). Accordingly, with V1 the value for the selected voxel of the first functional image data set, the group of differences between V1 to each of the values of the voxels within the box selected at 204 may be determined.

At 208, a second set of change metric values are determined. For example, with the first set of change metric values between a voxel of the first functional image data set and a box of voxels of the second functional image data set, the second set of change metric values may be between the corresponding voxel of the second functional image data set (e.g., a voxel in the second functional image data set corresponding to the voxel of the first functional image data set selected at 202, or a voxel in the second functional image data set having the same coordinates as the voxel selected at 202) and a box of voxels of the first functional image data set. Accordingly, at 208, the process discussed in connection with step 206 may be repeated after flipping the order of the data sets (i.e., at 208 the voxel is in the second functional image data set and the box is in the first functional image data set).

At 210 of the illustrated embodiment, an operator is applied on the first and second sets of change metric values (e.g., the values determined at 206 and 208). For example, the operator that is applied may include one or more of minimum or mean functions. At 212, a signal change is determined for the selected voxel coordinate based on the first and second sets of change metric values to which the operator has been applied. For example, the minimum of the absolute values of all calculated differences may be found, and a positive or negative signed difference value is determined corresponding to the found minimum value. That difference value may then be placed at the corresponding coordinate (e.g., the coordinate of the voxel selected at 202) in the local change map.

At 214, it is determined if all voxels to be analyzed have been considered. If there are additional voxels, the method 200 returns to 202 and another voxel is selected and processed or analyzed. If all voxels have been considered, then the method 200 proceeds to 216.

At 216, a volumetric map of the signal changes determined above is generated. For example, the local change map may be generated by using the values for each voxel coordinate determined at 212.

Figure 3:
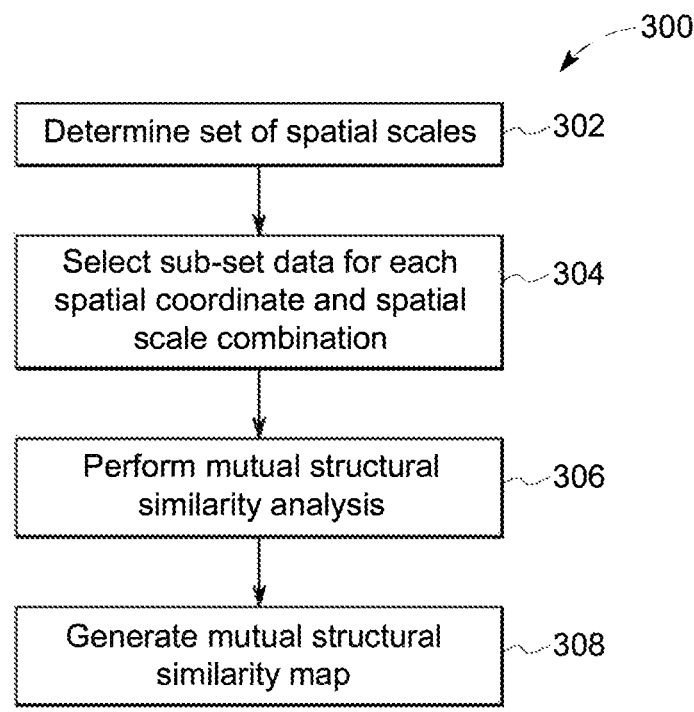
FIG. 3 shows a flowchart of a method, according to an embodiment.

FIG. 3 provides a flowchart of a method 300 for imaging in accordance with various embodiments (e.g., for generating a mutual structural similarity map for use in connection with method 100). The method 300 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be able to be used as one or more algorithms to direct hardware (e.g., one or more aspects of the processing unit 520) to perform one or more operations described herein.

At 302, a set of different spatial scales is determined. The set of different spatial scales are to be analyzed across an image volume (e.g., an image volume defined by a first or reference functional image data set and a second or follow-up functional image data set). Use of different scales allows for a mutual structural similarity analysis that considers possible or potential structures of different sizes. In various embodiments, the scales may range from a size of a few voxels to a size of about half the image size. In some embodiments, 16 or more different scales may be utilized. It may be noted that a selected spatial scale when used may be treated or understood as selecting a sub-set from the image data corresponding to a box (or square) with a side length equal to the spatial scale.

At 304, for each spatial coordinate (e.g., voxel) and spatial scale combination, sub-set data is selected. For example, first sub-set data may be selected from the first functional image data set and second sub-set data may be selected from the second functional image data set. Each spatial coordinate or voxel may be selected and analyzed in turn as part of processing the entire image volume. Accordingly, a first spatial coordinate or voxel may be selected, and processed or analyzed as discussed herein in combination with each selected spatial scale separately. Once all spatial scale combinations with that particular voxel have been analyzed, subsequent voxels may be similarly analyzed in turn. In various embodiments, the sub-set data is selected from the image data sets corresponding to a selected voxel (e.g., as a center of the sub-set) and the selected spatial scale (e.g., as a box dimension). Accordingly, first sub-set data may be selected for a voxel of the first functional image data set, and second sub-set data may be selected for a voxel of the second functional image data set, in connection with each of the selected spatial scales. In various embodiments, each scale is separately processed for each voxel.

At 306, a mutual structural similarity analysis is performed. The mutual structural similarity analysis in the illustrated embodiment is performed to determine mutual structural similarity values between the two image data sets for each particular spatial coordinate and spatial scale combination, based on or using the sub-set data (e.g., using the first sub-set data and second sub-set data for each coordinate/scale combination). In various embodiments, a mutual structural similarity metric may be based on a mutual information mathematical approach, or similar mathematical approach.

Generally, the mutual structural similarity analysis is calculated around each voxel and within a selected length scale (e.g., with the scale length defining the size of a box around the voxel). In some embodiments, for a given box of voxels, the image value data is extracted from the first functional image data set and the second functional image data set to form a first sub-set and a second sub-set, respectively. Then, a mathematical function is applied on the two sub-sets to calculate a metric that represents structural similarity and is not sensitive to the absolute values of the voxels. In such an approach, if the structure is very similar in the two sub-sets, the function response will be high, even if the absolute scales of the corresponding values are very different between the two sub-sets. One example technique that may be used to provide such an approach is known as a "mutual information" approach, which is based on entropies of co-occurrence histograms. For example, the mutual information (MI) of two sub-regions A and B may be expressed as $MI=H(A)+H(B)-H(A,B)$, where $H(A,B)=-SUM_{a,b}[P_{AB}(a,b)*\log(P_{AB}(a,b)]$; $H(X)=-SUM_x[P_x(x)*\log(P_x(x))]$; P is calculated as a histogram (self or joint), and H is the entropy function. Other mathematical techniques that may be employed for structural similarity analysis include, by way of example, wavelet-based local feature extraction or principle component analysis.

At 308, the mutual structural similarity map is generated using the mutual structural similarity analysis values. For example, in various embodiments, for each particular spatial coordinate, the mutual structural similarity analysis values for the corresponding spatial scales are weighted and combined to generate the mutual structural similarity map. The resulting map may also be referred to as a unified mutual structural similarity map. By way of example, the function $sum(M(i)/s(i)^p)$ may be employed to accomplish the combination, where M is the mutual information function response, s is the spatial length scale, and p is a predetermined parameter (e.g., which may be selected from the range 0.5 to 2.0). The sum is on all the length scale indexes "i."

Figure 4:
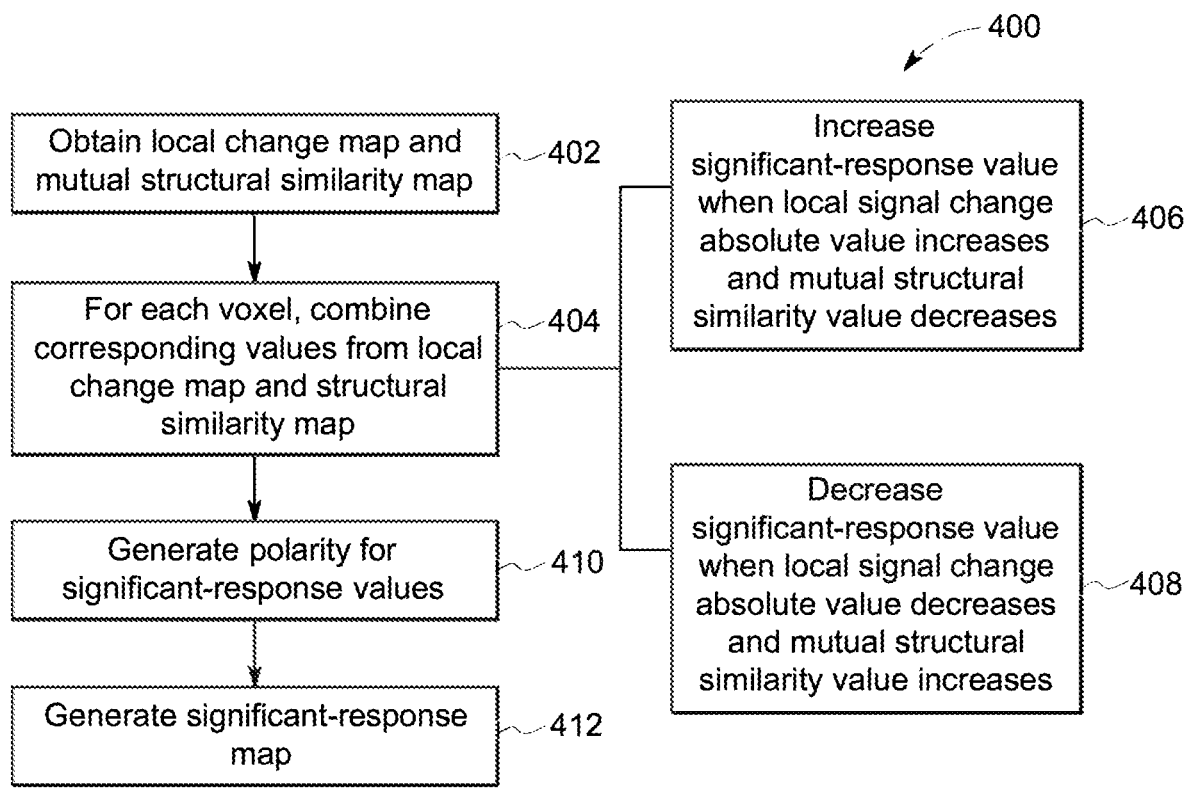
FIG. 4 shows a flowchart of a method, according to an embodiment.

FIG. 4 provides a flowchart of a method 400 for imaging in accordance with various embodiments (e.g., for generating a significant-response map for use in connection with method 100). The method 400 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware (e.g., one or more aspects of the processing unit 520) to perform one or more operations described herein.

At 402, a local change map and a mutual structural similarity map are obtained. The local change map and a mutual structural similarity map in various embodiments are for first and second functional image data sets as discussed herein, and may be determined using one or more aspects discussed herein in connection with FIG. 1, FIG. 2, and/or FIG. 3.

At 404, for each voxel, corresponding values from the local change map and the mutual structural similarity map are combined. In various embodiments, the corresponding values (e.g., values from each map for the same spatial coordinate or voxel) are combined to provide a significant-response value for the corresponding location (e.g., voxel) of the significant-response map. In various embodiments, relatively larger values of change of absolute value of local signals from the first functional imaging data set to the second functional imaging data set, and/or relatively smaller values of mutual structural similarity values between the first and second functional imaging data sets provides relatively higher significant-response values (e.g., corresponds to more relevant changes). On the other hand, relatively smaller values of change of absolute value of local signals from the first functional imaging data set to the second functional imaging data set, and/or relatively larger values of mutual structural similarity values between the first and second functional imaging data sets provides relatively lower significant-response values (e.g., corresponds to less relevant changes). In some embodiments, the combination is based on the logic shown at 406 and 408. At 406, the significant response value is increased when a corresponding local signal change absolute value increases and a corresponding mutual structural similarity value decreases. At 408, the significant response value is decreased when the corresponding local signal change absolute value decreases and a corresponding mutual structural similarity value increases. An increased or higher significant response value corresponds to a change that is of greater diagnostic interest, while a decreased or lower significant response value corresponds to a change that is of lesser diagnostic interest. The local change values and mutual structural similarity values may be weighted or scaled to help ensure that both are considered in determining the corresponding significant-response values.

At 410, a polarity for the significant response map values is generated. For example, in various embodiments, the polarity is positive where the corresponding local change map value is positive, and the polarity is negative where the corresponding local change map value is negative.

At 412, the significant-response map is generated from the values combined at 404 (e.g., using steps 406, 408, and 410). In various embodiments, a threshold may be used so that only sufficiently high significant-response values are displayed. Alternatively or additionally, shades of different colors may be assigned to ranges of significant-response values for convenient display and characterization of relative values throughout an image volume. Generally, the significant-response map, which is generated using the local change analysis as well as the mutual structural similarity analysis, is to show or highlight regions which significantly involve both activity changes and structural changes. For example, if liver uptake activity is very high in the first scan but is reduced to half as strong in the second scan (but still having significant activity), the absolute value difference in each voxel of the liver may be relatively high. However, if the liver uptake activity for both the first and second scan is distributed homogenously within the same liver structure, the structural analysis for those voxels will show high response, and the combined significant-response map will show no, small, or insignificant values for the liver (as determined using the logic of step 408 or similar, reducing the significant response value for a relatively high structural similarity). As another example, if a small lesion with relatively moderate activity uptake in the first scan has disappeared or is greatly reduced in the second scan, the combined significant-response map will show significant values because both image values and local structures were changed in way increasing the significant response value (as determined using the logic of step 406 or similar, providing increased significant response values for decreased structural similarity). Accordingly, in various embodiments, only those portions of an image having both meaningful activity changes and structural changes are displayed as having significant responses of particular diagnostic activity.

Figure 5:
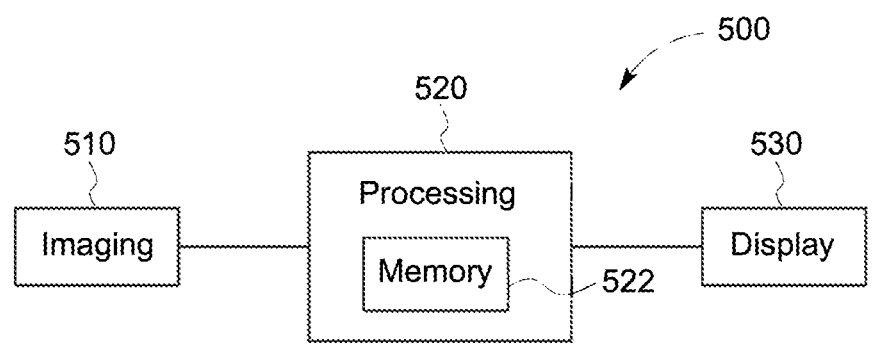
FIG. 5 provides a schematic view of an imaging system in accordance with an embodiment.

FIG. 5 provides a schematic view of an imaging system 500. The imaging system 500 includes an imaging detector system 510, a processing unit 520, and a display unit 530. In the illustrated embodiment, the imaging detector system 510 acquires imaging data (e.g., a first or reference functional image data set, along with one or more follow-up image data sets as discussed herein). The processing unit 520 acquires or obtains the imaging data from the imaging detector system 510 and uses the imaging data as discussed herein (e.g., in connection with one or more aspects of the methods discussed in connection with FIGS. 1-4) to generate a significant-response, which is displayed by the display unit 530. It may be noted that in some embodiments, the imaging system 500 may not include the imaging detector system 510, with the imaging data instead acquired from a separate or distinct imaging system and/or database.

The imaging detector system 510 in various embodiments includes one or more detector units configured to acquire functional imaging data. For example, in some embodiments, the imaging detector system is configured to acquire nuclear medicine (NM) imaging information, such as PET or SPECT imaging information. For example, a radiopharmaceutical may be administered to an object being imaged. Portions of the object being imaged then emit photons. The emissions from different portions of the object vary based on the uptake of the radiopharmaceutical by the corresponding portions. The imaging detector system 510 may then be used to acquire photon counts which may be used to reconstruct an image of the object. The imaging detector system 510 in various embodiments may be configured as a NM multi-head imaging system. (See, e.g., FIG. 7 and related discussion). It may be noted that other detector systems, such as PET, ultrasound, CT, or MRI may be used in other embodiments.

The depicted processing unit 520 of the example depicted in FIG. 5 is configured to acquire imaging information (e.g. first and second functional image data sets as discussed herein) and to determine which differences between the image data sets are more meaningful from a diagnostic point of view. The processing unit 520 in various embodiments is configured to perform one or more tasks or steps discussed in connection with FIG. 1, FIG. 2, FIG. 3, and/or FIG. 4. For example, the processing unit 520 in various embodiments obtains a first (or reference) functional image data set, and a second (or follow-up) functional image data set. The processing unit 520 then generates a local change map using the first functional image data set and the second functional image data set, generates a mutual structural similarity map using the first functional image data set and the second functional image data set, generates a significant-response map using the local change map and the mutual structural similarity map, and displays the significant-response map.

In various embodiments the processing unit 520 includes processing circuitry configured to perform one or more tasks, functions, or steps discussed herein. It may be noted that "processing unit" as used herein is not intended to necessarily be limited to a single processor or computer. For example, the processing unit 520 may include multiple processors, FPGA's, ASIC's and/or computers, which may be integrated in a common housing or unit, or which may distributed among various units or housings (e.g., one or more aspects of the processing unit 520 may be disposed in a separate physical unit or housing). It may be noted that operations performed by the processing unit 520 (e.g., operations corresponding to process flows or methods discussed herein, or aspects thereof) may be sufficiently complex that the operations may not be performed by a human being within a reasonable time period.

In the illustrated embodiment, the processing unit 520 includes a memory 522. Generally, the various aspects of the processing unit 520 act individually or cooperatively with other aspects to perform one or more aspects of the methods, steps, or processes discussed herein.

The memory 522 may include one or more computer readable storage media. The memory 522, for example, may store information describing previously determined parameters (e.g., weighting parameters), scale sizes, or the like. Further, the process flows and/or flowcharts discussed herein (or aspects thereof) may represent one or more sets of instructions that are stored in the memory 522 for direction of operations of the imaging system 500 (e.g., processing unit 520).

Figure 6:
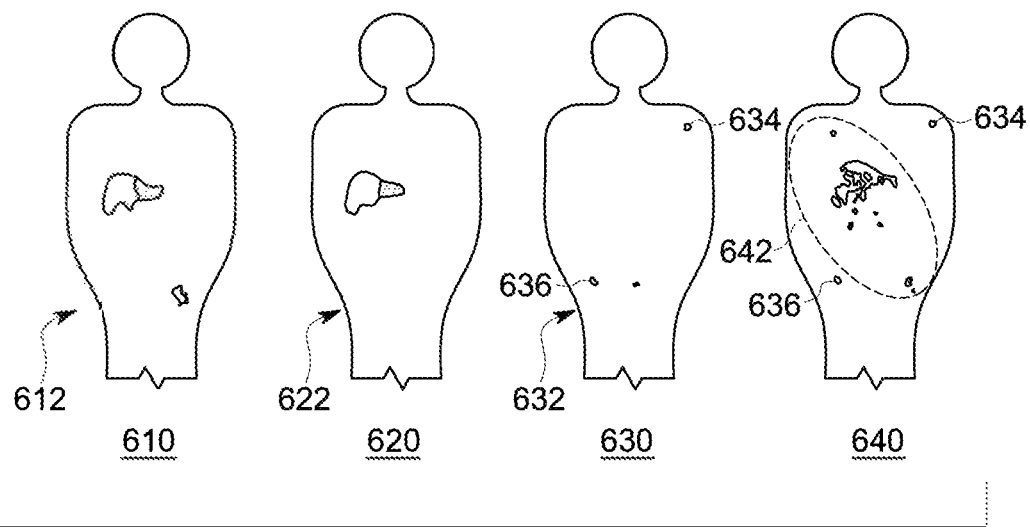
FIG. 6 provides example views of imaging displays in accordance with an embodiment.

FIG. 6 provides examples of displays that may be used in connection with various embodiments disclosed herein. The particular example of FIG. 6 relates planar scans taken with a SPECT system with Lu-177 radiotracer. Display 610 shows a baseline image 612 that has been reconstructed using functional image data from a first data acquisition. Display 620 shows a follow-up image 622 that has been reconstructed using functional image data from a second data acquisition taken after an elapsed treatment period from the first data acquisition. Comparison of the acquired imaging information may be used to evaluate the effectiveness of treatment undergone during the elapsed treatment period and/or to track progress or development of the patient. Display 640 shows a simple difference map that shows differences in activity level between the images displayed in display 610 (the reference or baseline image 612) and display 620 (the follow-up image 622).

However, display 640 includes a relatively large amount of changes in a first portion 642 that is unrelated to any structural changes. For improved diagnostic convenience and/or accuracy, using techniques disclosed herein, a significant-response map 632 may be generated that is shown on display 630. In the significant-response map 632, the changes shown in the first portion 642 of display 640 have been eliminated or de-emphasized (e.g., based on high mutual structural similarity in the first and second functional image data sets corresponding to the first portion 642. However, second portion 634 and third portion 636, which correspond to both activity and structural changes, are displayed via the significant-response map 632 of the display 630.

Figure 7:
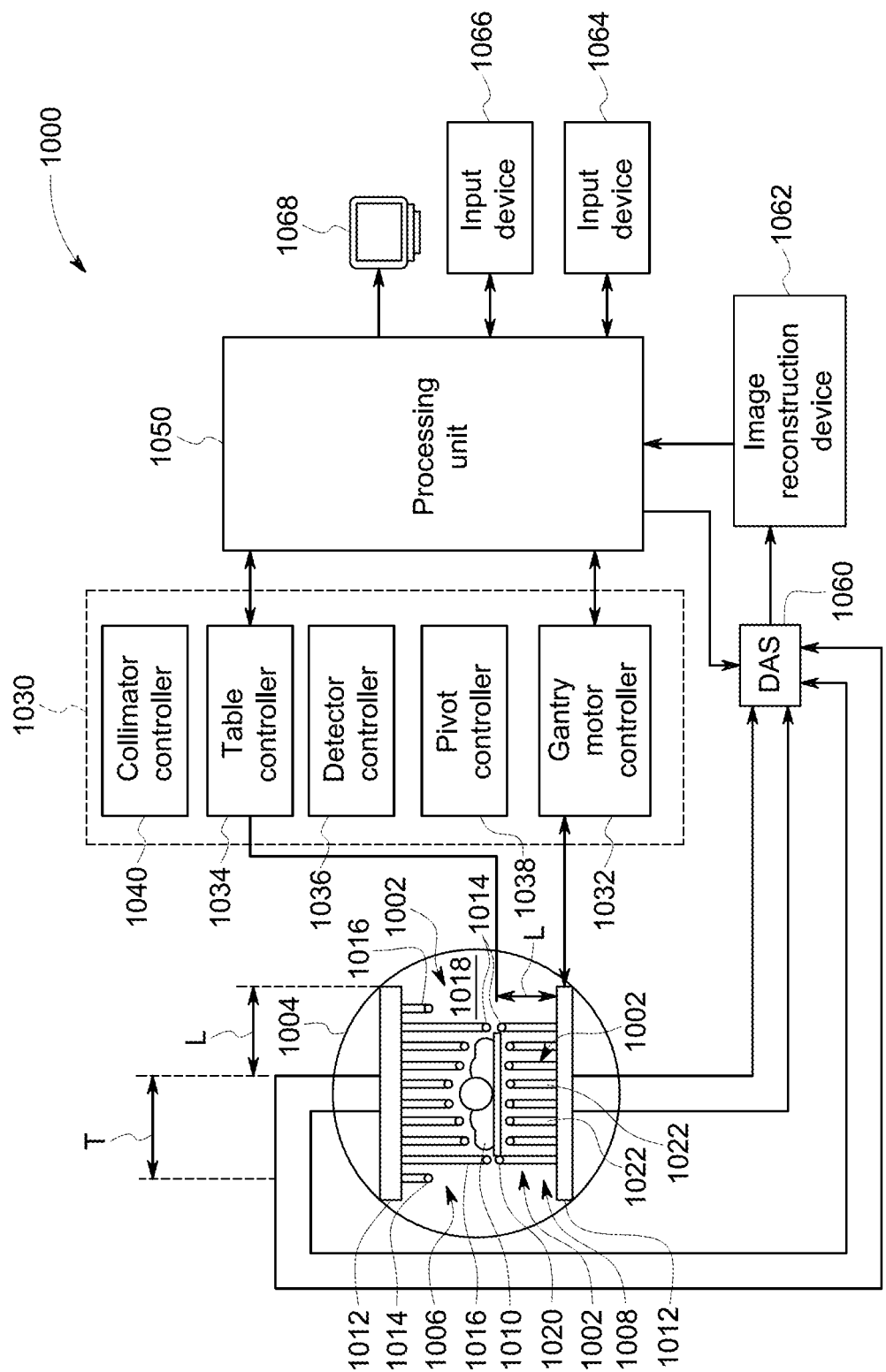
FIG. 7 shows a schematic view of an imaging system, according to an embodiment.

Embodiments described herein may be implemented in medical imaging systems, such as, for example, SPECT, SPECT-CT, PET and PET-CT. Various methods and/or systems (and/or aspects thereof) described herein may be implemented using a medical imaging system. For example, FIG. 7 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 7 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 7. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 7). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 7 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 7 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A method for follow-up functional imaging after obtaining a first functional image data set of a patient, the method comprising:
    obtaining a second functional image data set of the patient at a follow-up time subsequent to the obtaining of the first functional image data set;
    generating a local change map of functional image data using the first functional image data set and the second functional image data set;
    generating a mutual structural similarity map using the first functional image data set and the second functional image data set;
    generating a combined significant-response map using a combination of the local change map of functional image data and the mutual structural similarity map; and
    displaying the significant-response map.

2. The method of claim 1, wherein generating the local change map comprises:
    determining, for each voxel of the first functional image set, a first set of change metric values between a value of the voxel in the first functional image data set and values of neighboring voxels in the second functional image data set; and
    determining, for each voxel of the second functional image set, a second set of change metric values between a value of the voxel in the second functional image data set and values of neighboring voxels in the first functional image data set.

3. The method of claim 2, further comprising:
    applying an operator on the first and second sets of change metric values: and
    determining a signal change for each selected voxel coordinate based on the first and second sets of change metric values to which the operator has been applied.

4. The method of claim 1, further comprising determining mutual structural similarity analysis values across different spatial scales for the first functional image data set and the second functional image data set, and combining the mutual structural similarity analysis values of the different spatial scales to generate the mutual structural similarity map.

5. The method of claim 1, wherein generating the mutual structural similarity map comprises:
    determining a set of different spatial scales to be analyzed across an image volume;
    for each spatial coordinate and spatial scale combination, selecting sub-set data from the first functional imaging data set and the second functional imaging data set;
    performing a mutual structural similarity analysis to determine mutual structural similarity values for each particular spatial coordinate and spatial scale combination, based on the sub-set data; and
    weighting and combining, for each particular spatial coordinate, the mutual structural similarity analysis values for the corresponding spatial scales to generate the mutual structural similarity map.

6. The method of claim 1, wherein generating the significant-response map comprises:
    for each voxel, combining corresponding values from the local change map and the mutual structural similarity map; and
    generating the significant-response map from the combined values.

7. The method of claim 6, wherein combining the corresponding values comprises:
    increasing a significant-response value when a corresponding local signal change absolute value increases and a corresponding mutual structural similarity value decreases; and
    decreasing a significant-response value when the corresponding local signal change absolute value decreases and a corresponding mutual structural similarity value increases.

8. The method of claim 1, wherein the first functional imaging data and the second functional imaging data comprise one of single photon emission computed tomography (SPECT) imaging data or positron emission tomography (PET) imaging data.

9. The method of claim 1, further comprising:
    reconstructing a first image with the first functional imaging data;
    reconstructing a second image with the second function imaging data; and
    displaying the first image and the second image with the significant-response map.

10. An imaging system comprising:
    an imaging detector system configured to acquire a first functional image data set of a patient, and to acquire a second functional image data set of the patient at a follow-up time subsequent to the obtaining of the first functional image data set;
    at least one processor configured to:
        generate a local change map of functional image data using the first functional image data set and the second functional image data set;
        generate a mutual structural similarity map using the first functional image data set and the second functional image data set;
        generate a combined significant-response map using a combination of the local change map of functional image data and the mutual structural similarity map; and
    a display unit configured to display the significant-response map.

11. The system of claim 10, wherein the at least one processor is further configured to determine mutual structural similarity analysis values across different spatial scales for the first functional image data set and the second functional image data set, and to combine the mutual structural similarity analysis values of the different spatial scales to generate the mutual structural similarity map.

12. The system of claim 10, wherein the at least one processor is configured to generate the significant-response map by:
for each voxel, combining corresponding values from the local change map and the mutual structural similarity map; and
generating the significant-response map from the combined values.

13. The system of claim 12, wherein combining the corresponding values comprises:
increasing a significant-response value when a corresponding local signal change absolute value increases and a corresponding mutual structural similarity value decreases; and
decreasing a significant-response value when the corresponding local signal change absolute value decreases and a corresponding mutual structural similarity value increases.

14. The system of claim 10, wherein the imaging detector system is configured to acquire at least one of single photon emission computed tomography (SPECT) imaging data or positron emission tomography (PET) imaging data.

15. A non-transitory computer readable storage medium having stored thereon a computer program comprising instructions, which, when executed by a computer, cause the computer to:
obtain a first functional image data set of a patient from a first time;
obtain a second functional image data set of the patient at a follow-up time subsequent to the obtaining of the first functional image data set;
generate a local change map of functional image data using the first functional image data set and the second functional image data set;
generate a mutual structural similarity map using the first functional image data set and the second functional image data set;
generate a combined significant-response map using a combination of the local change map of functional image data and the mutual structural similarity map; and
display the significant-response map.

16. The non-transitory computer readable storage medium of claim 15, wherein the instructions cause the computer to generate the local change map by:
determining, for each voxel of the first functional image set, a first set of change metric values between a value of the voxel in the first functional image data set and values of neighboring voxels in the second functional image data set; and
determining, for each voxel of the second functional image set, a second set of change metric values between a value of the voxel in the second functional image data set and values of neighboring voxels in the first functional image data set.

17. The non-transitory computer readable storage medium of claim 15, wherein the instructions cause the computer to:
apply an operator on the first and second sets of change metric values: and
determine a signal change for each selected voxel coordinate based on the first and second sets of change metric values to which the operator has been applied.

18. The non-transitory computer readable storage medium of claim 15, wherein the instructions cause the computer to generate the mutual structural similarity map by:
determining a set of different spatial scales to be analyzed across an image volume;
for each spatial coordinate and spatial scale combination, selecting sub-set data from the first functional imaging data set and the second functional imaging data set;
performing a mutual structural similarity analysis to determine mutual structural similarity values for each particular spatial coordinate and spatial scale combination, based on the sub-set data; and
weighting and combining, for each particular spatial coordinate, the mutual structural similarity analysis values for the corresponding spatial scales to generate the mutual structural similarity map.

19. The non-transitory computer readable storage medium of claim 15, wherein the instructions cause the computer to generate the significant-response map by:
for each voxel, combining corresponding values from the local change map and the mutual structural similarity map; and
generating the significant-response map from the combined values.

20. The non-transitory computer readable storage medium of claim 19, wherein combining the corresponding values comprises:
increasing a significant-response value when a corresponding local signal change absolute value increases and a corresponding mutual structural similarity value decreases; and
decreasing a significant-response value when the corresponding local signal change absolute value decreases and a corresponding mutual structural similarity value increases.

* * * * *